United States Patent
Liu et al.

(10) Patent No.: US 6,962,772 B2
(45) Date of Patent: Nov. 8, 2005

(54) METHOD FOR MANUFACTURING 3-D HIGH ASPECT-RATIO MICRONEEDLE ARRAY DEVICE

(75) Inventors: Ming-Yueh Liu, Taipei (TW); Heng-Chun Huang, MiaoLi (TW); Jauh-Jung Yang, Taipei (TW); Kun-Chih Pan, TaiChung (TW)

(73) Assignee: Industrial Technology Research Inst., Hsinchu (TW)

( * ) Notice: Subject to any disclaimer, the term of this patent is extended or adjusted under 35 U.S.C. 154(b) by 227 days.

(21) Appl. No.: 10/329,449

(22) Filed: Dec. 27, 2002

(65) Prior Publication Data

US 2004/0126707 A1    Jul. 1, 2004

(51) Int. Cl.[7] ............................................. G03F 7/26
(52) U.S. Cl. ........................ 430/320; 430/323; 216/67; 604/191
(58) Field of Search ........................ 430/5, 312, 320, 430/321, 323, 325; 216/67–71, 11, 41, 75; 604/191

(56) References Cited

U.S. PATENT DOCUMENTS

| | | | |
|---|---|---|---|
| 5,543,253 A * | 8/1996 | Park et al. ...................... 430/5 |
| 5,982,545 A * | 11/1999 | Su ............................... 359/569 |
| 6,015,599 A * | 1/2000 | Keller et al. ............... 428/34.4 |
| 6,334,856 B1 | 1/2002 | Allen et al. ................. 604/191 |
| 6,406,638 B1 | 6/2002 | Stoeber et al. ............... 216/11 |
| 6,451,240 B1 * | 9/2002 | Sherman et al. ............ 264/504 |
| 6,558,361 B1 * | 5/2003 | Yeshurun ..................... 604/272 |
| 6,603,987 B2 * | 8/2003 | Whitson ...................... 600/345 |
| 6,629,949 B1 * | 10/2003 | Douglas ....................... 604/46 |
| 2003/0201241 A1 * | 10/2003 | Harker et al. .................. 216/2 |

* cited by examiner

*Primary Examiner*—Kathleen Duda
(74) *Attorney, Agent, or Firm*—Troxell Law Office, PLLC

(57) ABSTRACT

A method for manufacturing a 3-D high aspect-ratio microneedle array device, comprising steps of: providing a substrate, with a photoresist layer coated thereon; performing photolithography on the photoresist layer by using a graytone mask so as to form a patterned photoresist layer; performing high-selectivity etching on the patterned photoresist layer and the substrate by using inductively coupled plasma etching so as to transfer the pattern onto the substrate and form a structure; applying a material on the structure; and de-molding the structure from the substrate.

6 Claims, 8 Drawing Sheets

METHOD FOR MANUFACTURING 3-D HIGH ASPECT-RATIO MICRONEEDLE ARRAY DEVICE

BACKGROUND OF THE INVENTION

1. Field of the Invention

The present invention generally relates to a method for manufacturing a 3-D high aspect-ratio microneedle array device and, more particularly, to a method employing inductively coupled plasma gray-scale etching for pattern transfer so as to form a bio-soluble/digestible polymer microneedle array device with a variable bevel angle at the opening of each needle.

2. Description of the Prior Art

Recently, with the rapid development in biological technology and medical treatment, numerous drugs and therapeutic agents have been developed in the battle against disease and illness. However, a frequent limitation of these drugs is their delivery. Even though drugs are commonly administered orally as pills or capsules, many drugs cannot be effectively delivered in this manner, due to degradation in the gastrointestinal tract and/or elimination by the liver. Moreover, some drugs cannot effectively diffuse across the intestinal mucosa. Another common technique for delivering drugs across a biological barrier is the use of a needle, such as those used with standard syringes or catheters, to transport drugs across (through) the skin. While effective for this purpose, needles generally cause pain; local damage to the skin at the site of insertion; bleeding, which increases the risk of disease transmission; and a wound sufficiently large to be a site of infection. The withdrawal of bodily fluids, such as for diagnostic purposes, using a conventional needle has these same disadvantages. Needle techniques also generally require administration by one trained in its use. The needle technique also is undesirable for long term, controlled continuous drug delivery.

Therefore, the microneedle array device by using MEMS (micro electromechanical system) technology has attracted considerable attention. Prior arts such as U.S. Pat. No. 6,334,856 and U.S. Pat. No. 6,406,638 disclose a microneedle array device by using a semiconductor substrate, e.g., silicon, and semiconductor processing. FIG. 1A is a side view showing a prior art microneedle device inserted into human skin, and FIG. 1B provides an enlarged view of microneedles fabricated according to the prior art.

In FIG. 1A, the device 10 includes a substrate 11, from which a plurality of microneedles 12 protrude. Each of the microneedles 12 can be hollow and may include multiple compartments so as to contain one or more drugs to be delivered into human skin. The thickness of the substrate 11 is between about 1 $\mu$m and 1 cm, and the width of the substrate 11 is between about 1 mm and 10 cm. In FIG. 1, the height (or length) of the microneedles 12 generally is between about 1 $\mu$m and 1 mm. The diameter and length both affect pain as well as functional properties of the needles. Therefore, the "insertion depth" of the microneedles 12 is preferably less than about 100 $\mu$m, more preferably about 30 $\mu$m, so that insertion of the microneedles 12 into the skin through the stratum corneum 14 does not penetrate past the epidermis 16 into the dermis 18, thereby avoiding contacting nerves and reducing the potential for causing pain.

FIG. 2A to FIG. 2E are cross-sectional views showing a method for manufacturing a 3-D high aspect-ratio microneedle array device according to the prior art. In FIG. 2A, a semiconductor substrate 22 such as Si is provided. Conventional semiconductor processing steps such as photolithography and etching are employed. A patterned photoresist layer 24 is formed on the semiconductor substrate 22 to have a plurality of windows 26 (only one is shown in the drawing) exposing the semiconductor substrate 22, as shown in FIG. 2B. The semiconductor substrate 22 is anisotropically etched to form a plurality of channels 26' (only one is shown in the drawing) through its entire thickness, as shown in FIG. 2C. The semiconductor substrate 22 is then coated with a chromium layer 28 followed by a second photoresist layer 30 patterned so as to cover the channels 26' and form a circular mask for subsequent etching, as shown in FIG. 2D. The semiconductor substrate 22 is then etched by a standard etch to form the outer tapered walls 32 of the microneedle in FIG. 2E.

FIG. 3A to FIG. 3G are cross-sectional views showing another method for manufacturing a microneedle array device according to the prior art. In FIG. 3A, there is provided a semiconductor substrate 44 such as a <100> Si wafer, which is polished on both sides. The semiconductor substrate 44 is cleaned using standard techniques. The wafer is then oxidized, for example, using a horizontal atmospheric pressure reactor at a temperature of 1100° C. to form a front side oxide layer 46 and a back side oxide layer 48. A photoresist layer 50 is coated on the back side oxide layer 48 and then the back side of the substrate 44 is patterned using photolithography in order to define a plurality of back side openings 51 (only one is shown) of the channel within the needle, as shown in FIG. 3B. Deep reactive ion etch (DRIE) is performed on the openings 51 to form a channel 56 until it reaches the front side oxide layer 46 or at some small distance (e.g., 10 $\mu$m) before the oxide layer 46. This results in the structure of FIG. 3C. FIG. 3C illustrates a channel 56 formed within the semiconductor substrate 44. Note that the channel 56 is formed vertically within the substrate 44. A final step associated with the back side etch is to grow an oxide layer 62 on the wall of the channel 56 to protect the channel during subsequent processing steps. FIG. 3D illustrates a channel oxide layer 62 covering the wall of the channel 56. A front side pattern 63 formed on the front side oxide layer 46 defines the outer perimeter of the needle, as shown in FIG. 2E, which illustrates an etched oxide layer 46 and a front side photoresist layer 63. Then, a needle is created by isotropically under etching the pattern defined by the etched oxide layer 46 and front side photoresist layer 63 using isotropic deep reactive ion etch (DRIE) of the photoresist/oxide mask. The isotropic etching forms smooth side walls 66 sloping from a narrow circumference tip to a wide circumference base, as shown in FIG. 3F. Finally, the residual photoresist layer 63, oxide 46, portion 68 of the substrate, oxide 48 and oxide 62 are removed, resulting in a structure having an opening 70 parallel with the substrate, as shown in FIG. 3G.

In both of the two prior arts, Si is used as the starting material; therefore, the mircroneedle array is not bio-soluble/digestible. There are two major problems in these prior arts:

1. The bevel angle at the opening of each microneedle is limited by the semiconductor processing steps for forming the undercut profile; however, wet-etching is not stable for controlling the etching profile.

2. If the microneedle happen to break after being inserted into human skin, the broken piece will hurt the human body when it enters a tissue or an organ of the body since it is not bio-soluble/digestible.

Accordingly, there is need in providing a method for fabricating a 3-D high aspect ratio microneedle array device with a variable bevel angle at the opening of each needle by using a bio-soluble/digestible polymer.

SUMMARY OF THE INVENTION

In view of these problems, it is the primary object of the present invention to provide a method for fabricating a 3-D high aspect-ratio microneedle array device, employing a gray-tone mask such that the each microneedle has a variable aspect ratio as well as a variable bevel angle at the opening of each needle.

It is another object of the present invention to provide a method for fabricating a 3-D high aspect-ratio microneedle array device, employing a bio-soluble/digestible polymer such that the microneedle array device is bio-soluble/digestible.

It is still another object of the present invention to provide a method for fabricating a 3-D high aspect-ratio microneedle array device, employing a simplified manufacturing processing so as to reduce the cost.

In order to achieve the foregoing objects, the present invention provides a method for fabricating a 3-D high aspect-ratio microneedle array device, comprising steps of: providing a substrate, with a photoresist layer coated thereon; performing photolithography on the photoresist layer by using a gray-tone mask so as to form a patterned photoresist layer; performing high-selectivity etching on the patterned photoresist layer and the substrate by using inductively coupled plasma etching so as to transfer the pattern onto the substrate and form a structure; applying a material on the structure; and de-molding the structure from the substrate.

Other and further features, advantages and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms.

BRIEF DESCRIPTION OF THE DRAWINGS

The objects, spirits and advantages of the preferred embodiment of the present invention will be readily understood by the accompanying drawings and detailed descriptions, wherein.

DETAILED DESCRIPTION OF THE INVENTION

The present invention providing a method for manufacturing a 3-D high aspect-ratio microneedle array device can be exemplified by the preferred embodiments as described hereinafter.

Figure 1A:
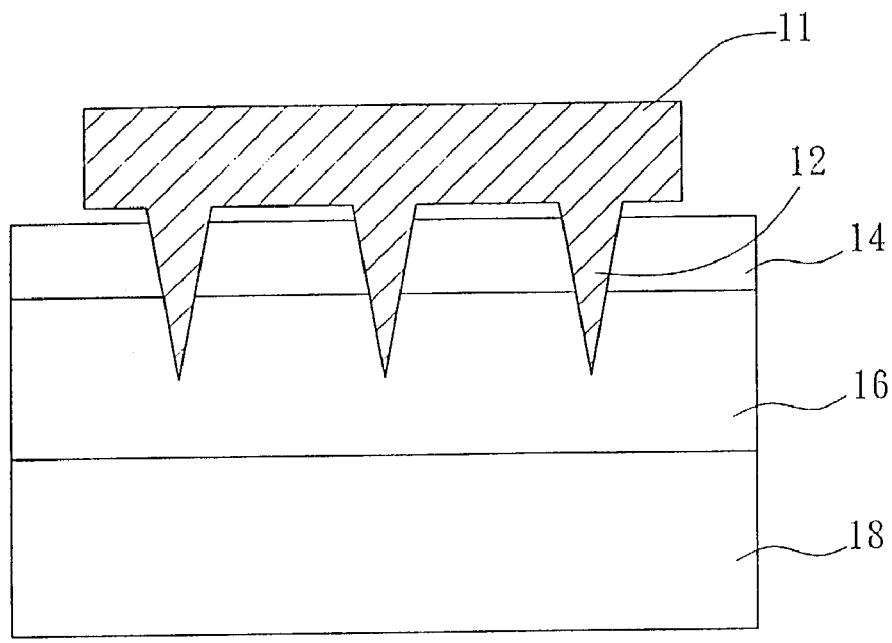
FIG. 1A is a side view showing a prior art microneedle device inserted into human skin.
Figure 1B:
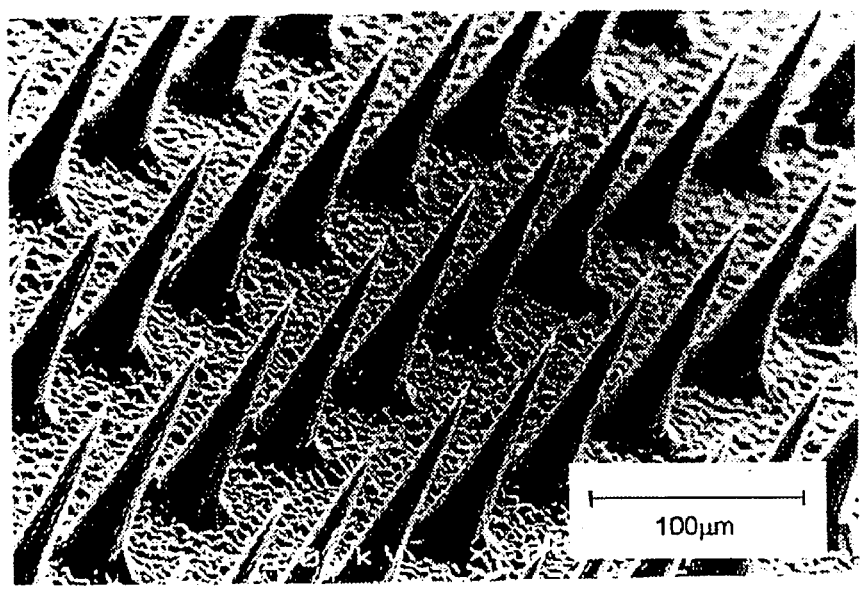
FIG. 1B is an enlarged view of microneedles fabricated according to the prior art.
Figure 2A:
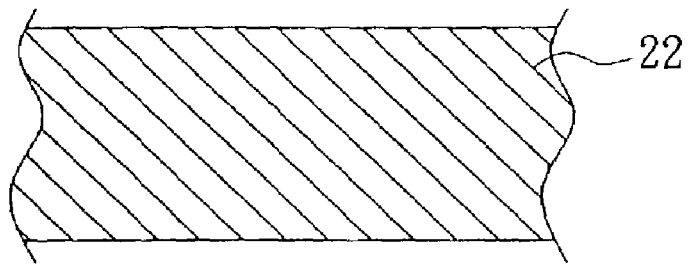
FIG. 2A to FIG. 2E are cross-sectional views showing a method for manufacturing a microneedle array device according to the prior art.
Figure 2B:
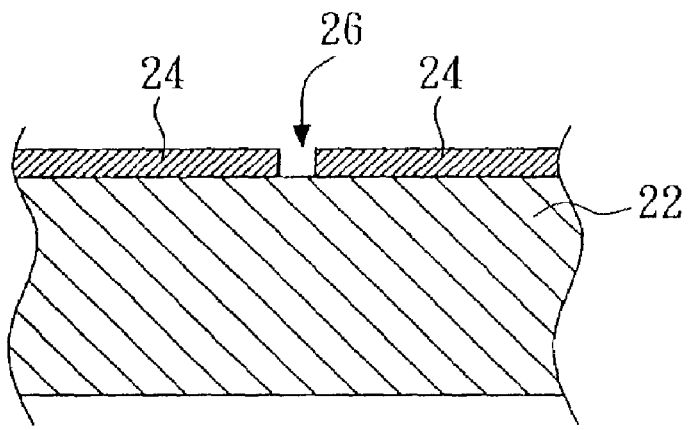
Figure 2C:
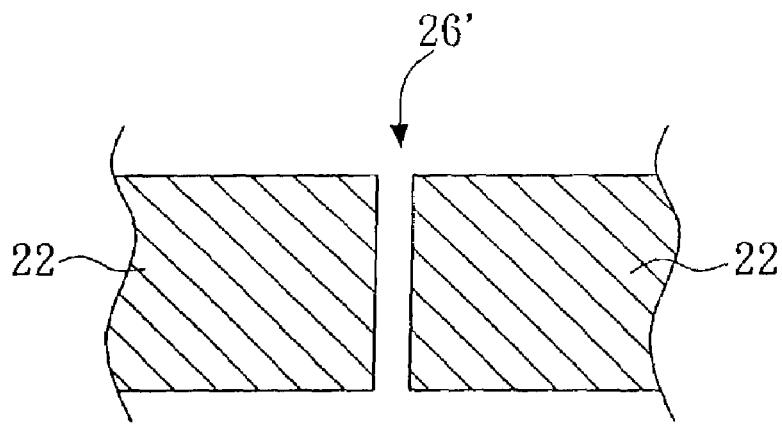
Figure 2D:
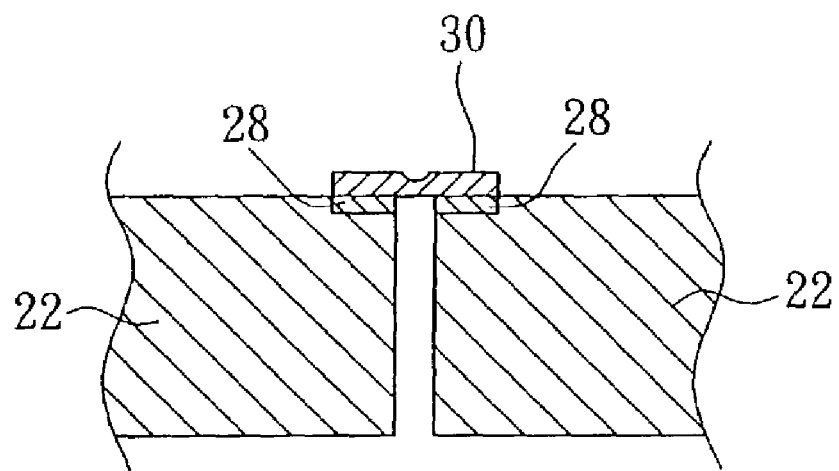
Figure 2E:
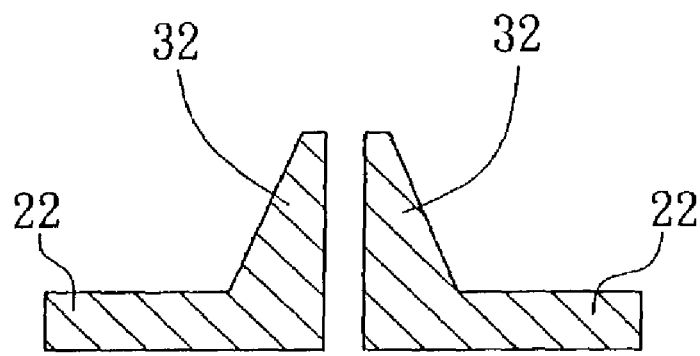
Figure 3A:
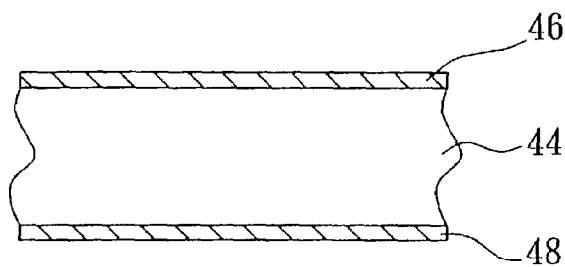
FIG. 3A to FIG. 3G are cross-sectional views showing a method for manufacturing a microneedle array device according to the prior art.
Figure 3B:
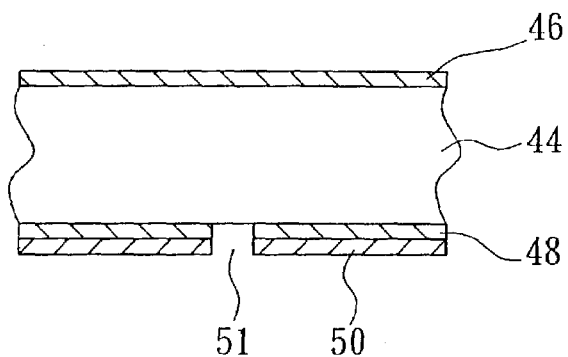
Figure 3C:
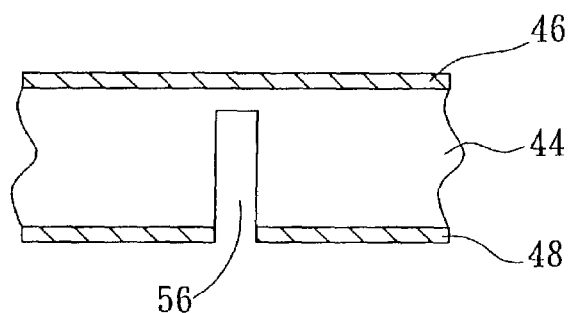
Figure 3D:
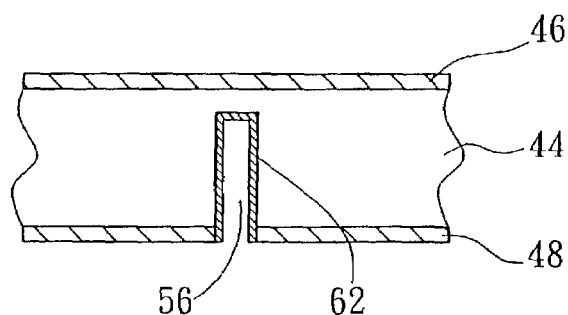
Figure 3E:
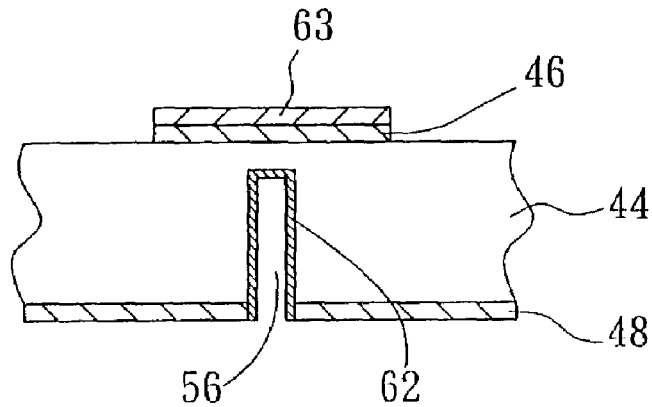
Figure 3F:
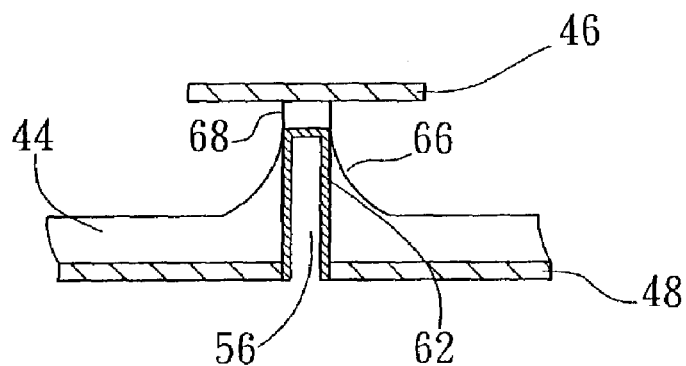
Figure 3G:
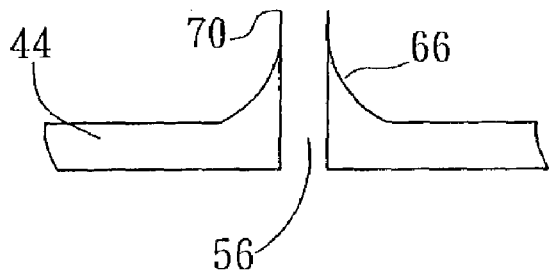
Figure 4A:
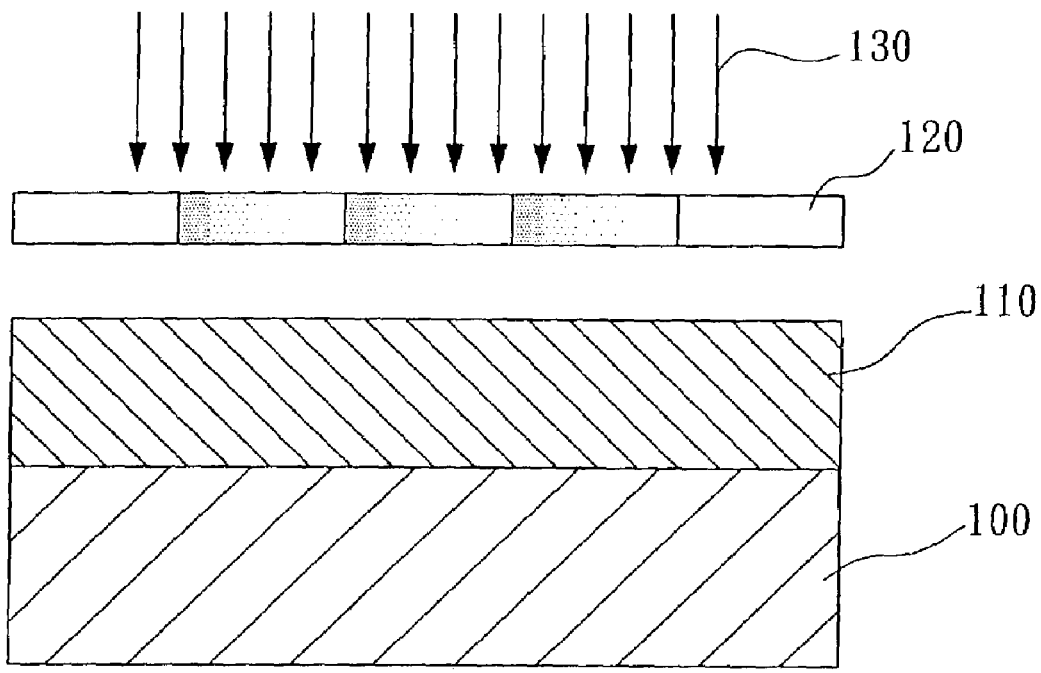
FIG. 4A to FIG. 4D are cross-sectional views showing a method for manufacturing 3-D high aspect-ratio microneedle array device according to the present invention.

Please refer to FIG. 4A to FIG. 4D, which are cross-sectional views showing a method for manufacturing 3-D high aspect-ratio microneedle array device according to the present invention. As shown in FIG. 4A, there is provided a semiconductor substrate 100 such as Si, which is coated with a photoresist layer 110. A gray-tone mask 120 is used to perform photolithography on the photoresist layer 110 on the substrate 100 by UV light 130. The gray-tone mask 120 is designed to have a pattern according to practical cases.

Figure 4B:
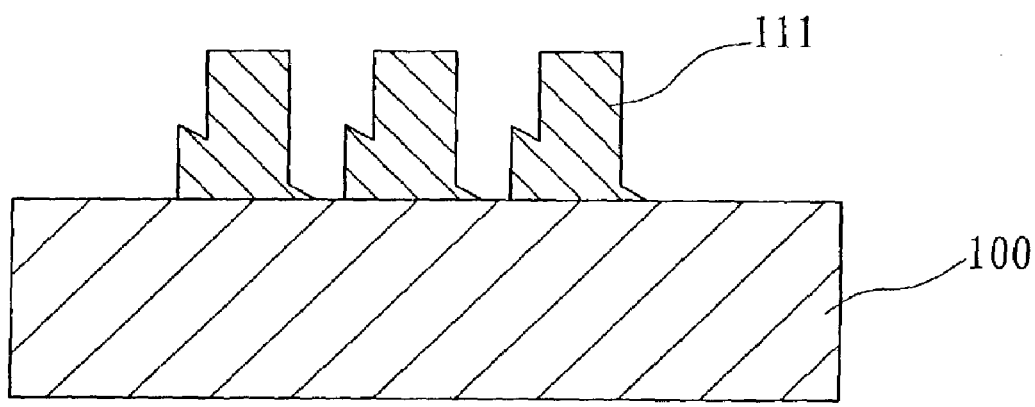
Figure 4C:
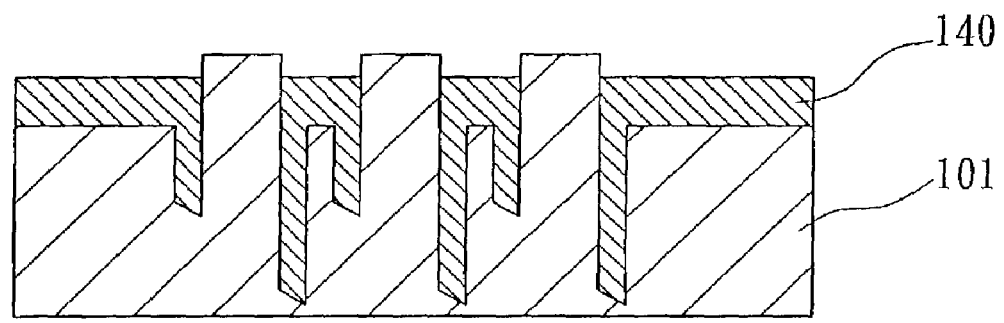
Figure 4D:
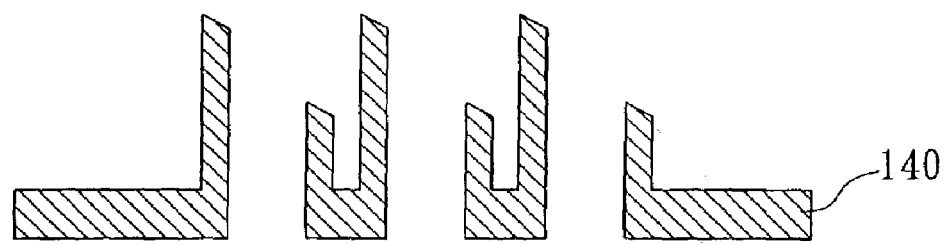

The photoresist layer 110 is then developed so as to form a pattern photoresist layer 111, as shown in FIG. 4B inductively coupled plasma (ICP) etching between Si and the photoresist, more particularly, Si:PR=1:50~70. Later, the patterned photoresist 111 together with the substrate 100 is etched by ICP etching such that a patterned substrate 101 is formed by pattern transfer from the patterned photoresist 111. Conventional hot-embossing or injection molding is used to apply a bio-soluble/digestible material 140, as shown in FIG. 4C. The bio-soluble/digestible material 140 is then de-molded so as to form a 3-D microneedle array device of the present invention, as shown in FIG. 4D.

In a preferred embodiment, the bio-soluble/digestible material 140 is a formed of poly glycolide co-lactide acid (PLGA), therefore the fabricated array device is bio-soluble/digestible.

Figure 5:
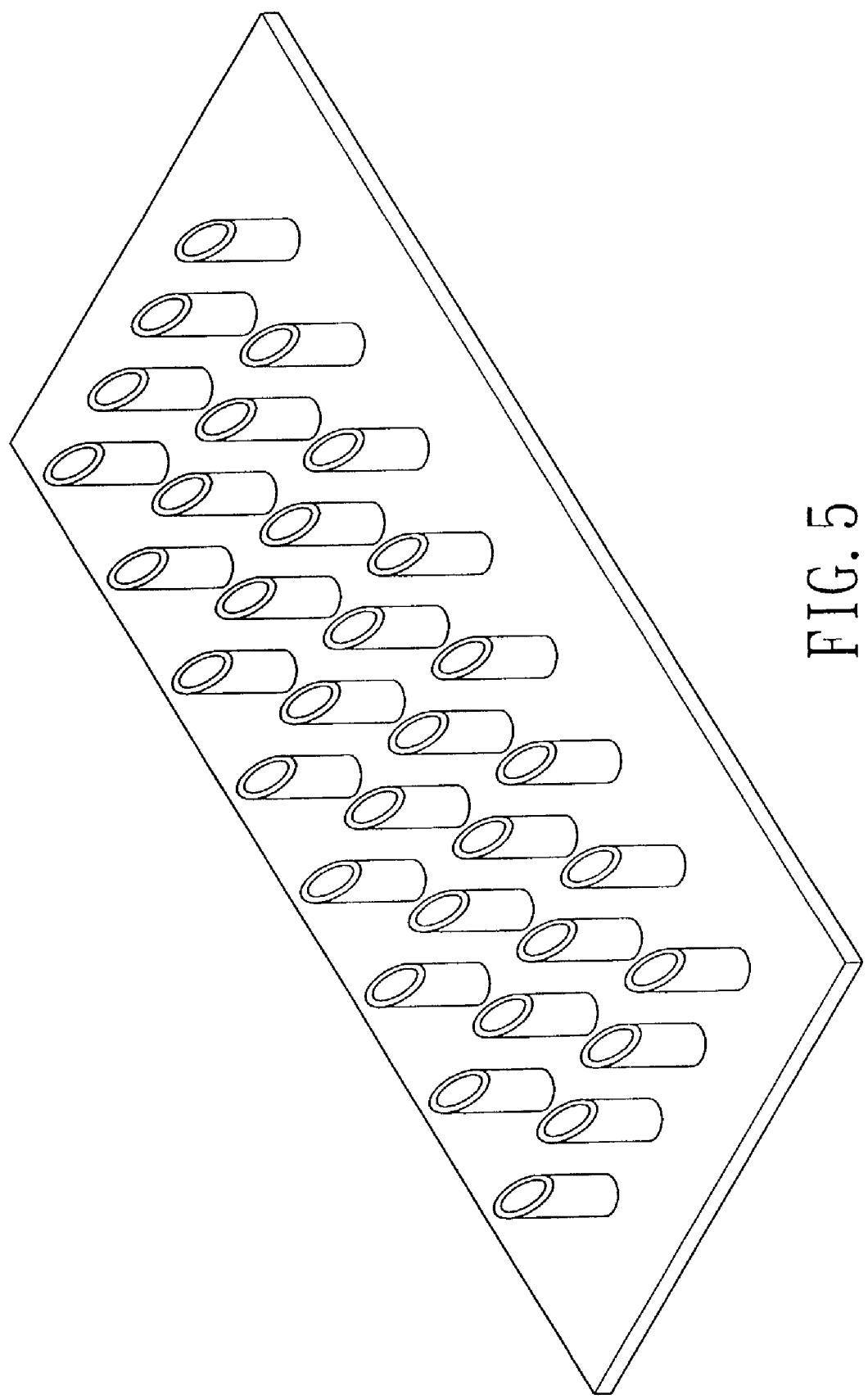
FIG. 5 is a perspective view of a 3-D high aspect-ratio microneedle array device according to the present invention.

On the other hand, the microneedle distribution, the aspect ratio and the bevel angle at the opening of each needle can be determined according to the pre-determined evaluations such as ICP etching selectivity ratio, etc. FIG. 5 is a perspective view of a 3-D high aspect-ratio microneedle array device according to the present invention.

According to the above discussion, the present invention discloses a method for manufacturing a 3-D high aspect-ratio microneedle array device. Therefore, the present invention has been examined to be novel, unobvious and useful.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A method for manufacturing 3-D high aspect-ratio microneedle array device, comprising steps of:
   a) providing a substrate, with a photoresist layer coated thereon;
   b) performing photolithography on said photoresist layer by using a gray-tone mask so as to form a patterned photoresist layer;
   c) performing high-selectivity etching on said patterned photoresist layer and said substrate by using inductively coupled plasma etching so as to transfer said pattern onto said substrate and form a mold-structure;
   d) applying a material on said mold-structure and forming a replicated molded-material structure; and e) de-molding said replicated molded-material structure from said mold-structure, wherein said replicated molded-material structure comprises:

a plurality of microneedles, each having a channel passing through its entire thickness;

wherein said plurality of microneedles exhibit an adjustable 3-D aspect ratio and have a variable bevel angle at an opening of each of said microneedles.

2. The method as recited in claim 1, wherein said step d) is performed by hot-embossing.

3. The method as recited in claim 1, wherein said step d) is performed by injection molding.

4. The method as recited in claim 1, wherein said plurality of microneedles are formed of poly glucolide co-lactide acid (PLGA).

5. The method as recited in claim 1, wherein said plurality of microneedles are bio-soluble.

6. The method as recited in claim 1, wherein said plurality of microneedles are bio-digestible.

* * * * *